United States Patent
Ritter

(10) Patent No.: US 10,946,132 B2
(45) Date of Patent: Mar. 16, 2021

(54) ACCESS CANNULA COMPRISING BLOCKING DEVICE

(71) Applicant: B. BRAUN AVITUM AG, Melsungen (DE)

(72) Inventor: Kai-Uwe Ritter, Melsungen (DE)

(73) Assignee: B. BRAUN AVITUM AG, Melsungen (DE)

(*) Notice: Subject to any disclaimer, the term of this patent is extended or adjusted under 35 U.S.C. 154(b) by 93 days.

(21) Appl. No.: 16/371,523

(22) Filed: Apr. 1, 2019

(65) Prior Publication Data

US 2019/0307944 A1   Oct. 10, 2019

(30) Foreign Application Priority Data

Apr. 9, 2018 (DE) .................. 10 2018 108 293.2

(51) Int. Cl.
| | | |
|---|---|---|
| *A61M 1/36* | (2006.01) | |
| *A61B 17/34* | (2006.01) | |
| *A61M 39/28* | (2006.01) | |
| *A61M 1/16* | (2006.01) | |

(52) U.S. Cl.
CPC ....... *A61M 1/3659* (2014.02); *A61B 17/3421* (2013.01); *A61M 1/3656* (2014.02); *A61M 39/28* (2013.01); *A61M 1/16* (2013.01); *A61M 1/3653* (2013.01); *A61M 1/3661* (2014.02); *A61M 2205/14* (2013.01); *A61M 2205/3331* (2013.01)

(58) Field of Classification Search
CPC .. A61M 1/3659; A61M 39/28; A61M 1/3656; A61M 2205/14; A61M 2205/3331; A61M 1/16; A61M 1/3653; A61M 1/3661; A61M 3/0279; A61M 5/00; A61M 5/1415; A61M 2005/1416; A61M 5/1454; A61M 39/281; A61M 39/288
See application file for complete search history.

(56) References Cited

U.S. PATENT DOCUMENTS

| | | | | |
|---|---|---|---|---|
| 3,029,059 A | * | 4/1962 | Hamilton | ............ A61M 39/288 251/9 |
| 5,807,333 A | * | 9/1998 | Osborne | ............... A61M 5/142 604/131 |
| 2006/0016478 A1 | | 1/2006 | Chantalat | |
| 2008/0281276 A1 | | 11/2008 | Shekalim | |

(Continued)

FOREIGN PATENT DOCUMENTS

WO     9711296 A1    3/1997

OTHER PUBLICATIONS

German Search Report for German Application No. 10 2018 108 293.2, with English translation, dated Nov. 29, 2018—16 pages.

(Continued)

*Primary Examiner* — Amber R Stiles
*Assistant Examiner* — Joshua Parker Reddington

(57) ABSTRACT

An access cannula which includes a dwell tube that serves as an access during treatment. A blocking device that maintains the dwell tube kinked in an idle position. In the idle position, the dwell tube is maintained kinked, preferably at a predetermined kink point that corresponds to a position in which a force exerted by the blocking device upon the dwell tube, the elastic reset force of the dwell tube and, where appropriate, a pressure prevailing in the dwell tube, balance one another.

17 Claims, 2 Drawing Sheets

(56) References Cited

U.S. PATENT DOCUMENTS

Figure 1:
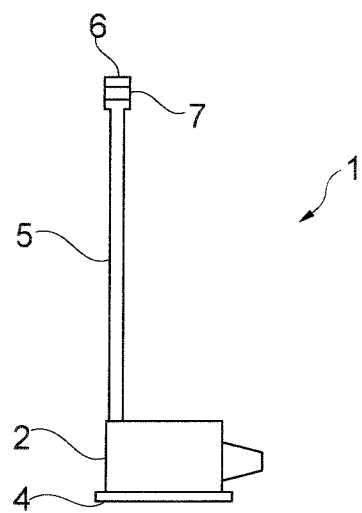

| | | | |
|---|---|---|---|
| 2010/0234809 A1* | 9/2010 | Kenley | F16K 7/06 |
| | | | 604/180 |
| 2011/0224601 A1 | 9/2011 | Shekalim | |
| 2013/0150680 A1 | 6/2013 | Larson et al. | |
| 2014/0194854 A1 | 7/2014 | Tsals | |
| 2017/0021098 A1* | 1/2017 | Rousche | A61M 5/16813 |

OTHER PUBLICATIONS

Extended European Search Report for European Application No. 19 167 973.7, dated Aug. 28, 2019, with translation, 13 pages.

* cited by examiner

ACCESS CANNULA COMPRISING BLOCKING DEVICE

RELATED APPLICATIONS

This application is related to and claims the benefit of priority under 35 U.S.C. § 119 of German Application No. 10 2018 108 293.2, filed Apr. 9, 2018, the content of which is incorporated by reference herein in its entirety.

FIELD

The present invention relates to an access cannula, especially a venous dwell cannula, comprising a dwell tube which is configured to serve as an access during treatment, especially dialysis treatment, wherein a blocking device is provided for maintaining the dwell tube kinked in an idle position.

BACKGROUND

Dialysis, especially hemodialysis, hemofiltration and hemodiafiltration, constitutes the most frequent type of treatment in the case of renal insufficiency and requires frequent and regular treatments for a patient which can be carried out both in hospital and at home on the patient's own.

For dialysis treatment, an arterial access is laid by means of an arterial insertion needle and a venous access is laid by means of a venous insertion needle to connect the patient to a dialysis machine. For this purpose, venous dwell cannulas or catheters are used in which a synthetic tube or dwell tube is introduced to a patient's vessel via an insertion needle or a metallic cannula and, after removing the insertion needle, remains in the vein as an access. Said venous dwell cannulas are sufficiently known from the state of the art.

If during dialysis treatment the venous access detaches and slips out of the vessel, this is referred to as venous needle dislocation (VND) representing a critical complication and risk for the patient. In such event, blood that has flown through the dialysis machine does not flow back to the patient's circulation but is pumped into the environment, especially by a blood pump of the treatment machine. In the case of VDN, an average patient may lose up to 50% of his/her total blood volume within 5 minutes, and only two minutes are sufficient until vital indications of a patient are significantly impaired. Consequently, it is essential that VND is detected as quickly as possible. Depending on the reaction time, the consequences range from relatively small loss of blood, increased risk of infection, and/or irreversible brain damage to death. Apart from the physical and psychological consequences for the patient, high expenses are also incurred due to required blood conserves and subsequent treatments. Especially in the case of home dialysis and treatments at night when the patients usually are asleep, VND is critical to catch, as the patients themselves are not able to notice the VND and possibly cannot react and draw attention to themselves in time.

It is a particular challenge that VND may occur almost at any time. Although several risk factors such as restlessness or mental impairment of the patients as well as the occurrence of myospasms during the treatment are known, VND also occurs in ideal conditions and thus can hardly be predicted, however.

For reducing the risk of VND there are guidelines concerning the way in which an access is to be laid and fixed. Furthermore, there exist solutions that can detect occurrence of VND and trigger an alarm as well as, where necessary, stop the blood pump of the treatment machine.

One solution is a pressure monitoring at the venous line and, at the venous access which is provided as a standard in dialysis machines. However, the monitoring of the venous pressure curve is deemed to be notoriously unsafe, inter alia because the pressure may strongly vary in response to a plurality of factors. Frequently, VND is detected delayed in time only, therefore the patient may have lost a significant amount of blood until the alarm is triggered. Furthermore, due to flow resistances at the needle or at the fixing material thereof as well as with incomplete release of the needle, for example, the pressure drop may happen to be so small that it is not detected as VND and no alarm is triggered at all.

Another solution consists in detecting leakage by leakage or moisture sensors disposed at the access which monitor blood loss into the environment, such as leak detection sensors marketed under the trademark VENACC™ by Fresenius Medical Care and leak detection sensors marketed under the trademark REDSENSE™ by Redsense Medical having a single-use sensor pad that is affixed together with the needle and detects already small amounts of leaking fluids. However, said devices involve additional expenses, as costly auxiliary devices and disposables are required for this purpose and human errors cannot be excluded in this way.

Thus, the known solutions do not allow for a one hundred percent safe detection of VND. Since by misuse or improper operation or too narrow limit values the probability of false alarms moreover is high, venous alarms frequently are simply cancelled so that VND might not be detected in time despite sounding of an alarm.

SUMMARY

Hence, it is the object of the present invention to provide a system which, inter alia, eliminates the afore-mentioned drawbacks of existing systems and especially enables VND to be reliably and quickly detected and the blood flow to be interrupted as quickly and reliably as possible. Furthermore, it is the object of the invention to provide such system which does not require any additional expenditure in terms of apparatuses and which is inexpensive and easy to handle.

This object is achieved by an access cannula, especially a venous dwell cannula/indwelling venous cannula/permanent venous cannula, comprising a dwell tube configured to serve as an access to a patient's body during treatment, especially dialysis treatment. Therein, a blocking device is provided which is configured to maintain the dwell tube kinked in an idle position (in which the dwell tube is not or not correctly applied in the patient's body).

The access cannula according to the invention is provided especially for laying the venous access, but it may equally be used also for the arterial access. Furthermore, the invention is not intended to be restricted to dialysis treatments. For example, use is also imaginable as an access for an infusion, where an access cannula according to the invention enables preventing drugs etc. from leaking in the case of needle dislocation. This is relevant especially to drugs for oncological treatment.

The idle position in which the dwell tube is maintained kinked preferably at a predetermined kink point corresponds to a position in which a force exerted by the blocking device upon the dwell tube, the elastic reset force of the dwell tube and, where appropriate, a pressure prevailing in the dwell tube are balancing each other.

In order to be capable of serving as an access, the access cannula including the dwell tube has to be maintained at a substantially or almost stretched position contrary to the force of the blocking device, for example by adhesive fixing to a patient's skin by a fixing base or pad provided at the access cannula, so that blood flow through the tube preferably without resistance is possible. Since, when laying the access as already afore-described, the dwell tube is pushed over an insertion needle and thus is inserted into the vein, the dwell tube follows the geometry of the insertion needle, i.e. it is stretched. Subsequently, the dwell tube can be fixed at said position to the patient's body and the insertion needle can be withdrawn. Hence, during standard laying of the access, the tube is maintained stretched by the needle, thus the need of any additional parts or movements/manipulation being prevented and the use of an access cannula according to the invention as compared to a common access cannula entailing no additional expenditure for the medical staff.

If the dwell tube slips out of the patient's vein, i.e. if a needle dislocation occurs, then also the attachment/fixing of the access cannula to the patient will detach. Consequently, the dwell tube is no longer kept in a stretched position and is kinked by the blocking device. This will interrupt or inhibit the blood flow through the treatment system, e.g. the dialysis machine, so that no or little blood can flow out of the dwell tube. Especially in the case of VND, viz. a needle dislocation at the venous access, in the most favorable case blood is prevented from being pumped out of the arterial access through the treatment system and out of the detached venous access into the environment.

Blocking the blood flow in an extracorporeal blood circulation of a dialysis machine, for example, results in increased blood pressure upstream of the kink when the venous access is blocked and results in decreasing blood pressure downstream of the kink when the arterial access is blocked. Said pressure change occurs quickly and is sufficient to be safely detected by the pressure monitoring system provided as a standard in the treatment system, especially the dialysis machine, and for a reaction to be initiated, i.e. for an alarm to be directly triggered and, where necessary, for a blood pump to be switched off or stopped, respectively. It is of particular advantage here that although an alarm can be cancelled, said alarm would immediately sound again due to the blocking of the blood flow.

It is noted that in the case of VND the force by which the blocking device maintains the tube kinked does not only act against the elastic reset force of the tube but also against the pressure built up by the blood pump, as the case may be. Accordingly, on the one hand the blocking device is adjusted or adjustable in response to a capacity of the blood pump employed so that re-opening of the dwell tube due to the increasing blood pressure is prevented or at least delayed for a predetermined period of time. On the other hand, the blocking device must be adjusted so that, in the case of a dwell tube adhesively attached to the patient's skin in a stretched state, said adhering cannot be undone by the blocking device itself, which would result in an interruption of the treatment and, in the worst case, might even trigger VND.

According to a preferred aspect of the invention, the blocking device includes a spring element which is disposed by a first end at a first position of the dwell tube and which is connected or connectable by a second end to the dwell tube at a second position. The second position is distanced from the first position at a distance along a longitudinal axis of the dwell tube. According to another preferred aspect of the invention, the distance and the spring element are set so that the spring element is tensioned when the dwell tube is maintained in a stretched position.

The spring element serves for exerting a (bending) force/spring force upon the dwell tube, thus causing the latter to be kinked. The spring force corresponds to the force of the blocking device. The spring element is slightly biased even in the idle position due to the distance of the first and second positions and/or due to the reset force of the dwell tube and in the stretched position is additionally tensioned beyond the bias of the idle position. Basically, it is also imaginable to provide plural spring elements. The distance may be defined by the positions of the connections of the blocking device to the dwell tube or may be defined due to different structural parameters such as the length of the spring. The first position may be located both distally and proximally from the second position. The first position or the second position may be the position at which the fixing base or the fixing pad is provided for adhesive fixing of the dwell tube to the patient's skin. The distance is set such that the spring force exerted on the dwell tube is a predetermined spring force which is dependent, as afore-described, for example on the capacity of the blood pump and/or on the stretched fastening of the dwell tube. The distance preferably is a fixedly set distance which is dependent, inter alia, on the length of the spring element or alternatively is directly determined by parameters of the spring element. However, it is also imaginable that the distance of the first and second positions can be set and secured, as either of the two positions is variable vis-à-vis the other one. This can be realized, for example, by the fact that one element which connects the spring element to the dwell tube is movable along the dwell tube, or that along the dwell tube plural elements for holding/connecting either of the ends of the spring element are provided and the respective end of the spring element can be repositioned or re-hooked, i.e. depending on the desired force/spring force of the blocking element the spring element can be held by different elements.

According to a preferred aspect of the invention, the spring element at the second position exerts a spring force upon the dwell tube which at least in part acts normal to the longitudinal axis of the dwell tube when the spring element is tensioned.

This allows to kink the dwell tube with relatively small effort, as compared to a case in which force would be applied to the dwell tube only in the longitudinal direction and the dwell tube would have to yield similarly to a pressurized kink rod. The spring force exerted by the spring element can act exclusively normal to the longitudinal axis of the dwell tube, however instead it may also be composed both of a vertical force component and of a force component in parallel to the longitudinal axis of the dwell tube. Since the spring element is attached to a first position of the dwell tube, this causes a moment which acts on the dwell tube and results in kinking.

According to a preferred aspect of the invention, the dwell tube is kinked by a spring force of the spring element preferably at a desired kink point, unless the dwell tube is maintained in a stretched position.

In other words, the spring force of the spring element is set such that the dwell tube is always kinked, unless a stretched position is specifically brought about. Even if, for example, VND occurs and an arm of the patient rests on the dwell tube, the dwell tube tends to turn away rather than stretch so that the dwell tube maintains its kinked position or its idle position. A stretched position of the dwell tube thus should be brought about only when both positions at which the ends of the spring element are fastened are specifically held and, where necessary, fixed such that the tube is stretched.

According to another preferred aspect of the invention, the blocking device includes a base portion directly or indirectly connecting or rendering connectable the first end of the spring element to the dwell tube, and includes a fitting portion connecting or rendering connectable the second end of the spring element to the dwell tube.

In the event when the first position and the second position can be set/varied relative to each other, the base portion and/or the fitting portion can be moved and, where necessary, secured on the dwell tube or may include plural differently positioned elements which are adapted to hold one end of the spring element. A movable base or fitting portion can be, for example, a closed or slit, preferably clip-on sleeve or a ring, e.g. a rubber ring, which can be displaced and, where appropriate, clamped along the tube, where necessary. Elements holding one end of the spring element can be, for example, hooks, eyes, grooves or undercuts. If the distance of the two positions relative to each other cannot be set, the base portion and/or the fitting portion can be tightly connected or connectable to the dwell tube. Furthermore, the base portion may be freely aligned with the remaining access cannula. For example, the side of the base portion to which the spring element is connected or fastened (here referred to as "top") may be radially opposed to the side at which the fixing base or pad of the access cannula is located (here referred to as "bottom"). Alternatively, the base portion may be aligned, however, at any angle with the access cannula, for example rotated about 90° vis-à-vis the alignment of the foregoing example, so that the spring element is located "laterally" from the base portion and the side at which the fixing base or pad of the access cannula may be located is "at the bottom".

According to a preferred aspect of the invention, at least the base portion and/or the fitting portion, preferably the entire blocking device including the spring element, are formed integrally with the dwell tube or are formed integrally as a component different from the dwell tube, preferably as an injection-molded part.

In this way, it is possible to manufacture the access cannula at low cost as a disposable. If the blocking device is manufactured or injection-molded separately from the dwell tube, it can be connected, e.g. glued, to the dwell tube in a further manufacturing step. The blocking device may be manufactured, where appropriate, integrally with other parts of the access cannula such as the fixing base or pad. In this way, the dwell tube may be a purchased part. This is equally possible when the blocking device or parts of the blocking device is/are injection-molded directly onto the dwell tube and thus is/are formed integrally with the latter.

According to a preferred aspect of the invention, the spring element is in the form of a flexible/bending spring.

This represents an embodiment of the invention and is especially advantageous, as the entire blocking device and, where necessary, even the entire access cannula including the dwell tube can be integrally formed, especially injection-molded, and thus can be manufactured at especially low cost. The bending spring may be, for example, in the form of a leaf spring, a flexible/bending beam or a flexible/bending rod. In order to render the blocking device ready for use or to put it in the idle position, the bending spring may be bent (tensioned) in another manufacturing step. For this purpose, e.g. the fitting portion can be connected to the dwell tube at the second position. Preferably, according to any one of the afore-described aspects of the invention, the fitting portion can be freely movable along the longitudinal axis of the dwell tube so that the position of the fitting portion (the second position) and the distance thereof from the first position is predetermined by the length of the bending spring. The fitting portion may be both connected or connectable pivotally (for instance rotatably about an axis normal to the longitudinal axis of the dwell tube) and/or movably to the dwell tube and connected or connectable tightly to the dwell tube, e.g. by gluing. A rotationally fixed connection between the bending spring and the dwell tube results in the fact that the angle at which the spring force acts on the dwell tube always is constant. Especially, if the bending spring forms a rigid right angle with the longitudinal axis of the dwell tube at the joint between the bending spring and the dwell tube, strictly speaking the spring force of the bending spring includes no component which is normal to the longitudinal axis of the dwell tube. However, the moment applied to the dwell tube by the bending spring directly results in the fact that part of the dwell tube moves in a direction normal to the longitudinal axis of the dwell tube, when it moves out of its stretched position. This entails kinking of the dwell tube. In the context of the present invention, this may be considered a force acting normal to the longitudinal axis of the dwell tube according to any one of the afore-described aspects of the invention.

According to a preferred aspect of the invention, the spring element is in the form of a tension spring, preferably of an elastic strip.

This constitutes a further embodiment of the invention. The tension spring is retained or hooked at its one end at the base portion and is retained or hooked at its second end at the fitting portion. Therein, the base portion defines a radial distance of the first end of the spring element from the longitudinal axis of the dwell tube. Where necessary, the base portion for this purpose has a rod-shaped part or is cam-shaped or has an appropriately large total diameter, however each structure extending radially outwardly starting from the longitudinal axis of the dwell tube may equally be used to define the radial distance of the first end of the spring element from the longitudinal axis of the dwell tube. Instead of an elastic strip, the tension spring may also be a spiral spring or the like, for example. The base portion and the fitting portion may be manufactured integrally with the dwell tube, especially attached by injection-molding to the latter, and are connected directly to the latter. Of preference, the second position of the dwell tube and the fitting portion are movable along the longitudinal axis of the dwell tube, wherein a minimum distance from the first position and from the base portion is defined e.g. by a stop. The force/spring force of the blocking device can be set, where necessary, by the fact that the spring element is exchanged for another spring element of different strength and/or that the fitting portion and/or the base portion according to any one of the afore-described aspects of the invention include plural selectable differently positioned elements for holding either of the ends of the spring.

According to a preferred aspect of the invention, the base portion is configured such that the first end of the spring element in the form of a tension spring is connected or connectable to the base portion at a predetermined radial distance from the longitudinal axis of the dwell tube.

The angle of the tension spring with the longitudinal axis of the dwell tube is dependent, according to this aspect of the invention, on the predetermined radial distance. Consequently, also the vertical force component of the spring force acting normal to the longitudinal axis of the dwell tube is dependent on the predetermined radial distance. Accordingly, the radial distance is selected to be sufficiently small so that the base portion is not in the way and the risk of getting stuck on the same is low but high enough for the vertical force component to be sufficiently high to kink the dwell tube in accordance with the invention.

Especially and preferably, the object is achieved by an access cannula in which at the first position the dwell tube includes a fixing base or a fixing pad which is configured for preferably affixing the dwell tube to a surface of the patient, preferably the patient's skin, and at which the spring element is fixed or held at the first end thereof, and at the second position the dwell tube includes a fitting element or a fitting portion at which the spring element is fixed or held at the second end thereof, with the dwell tube being axially formed between the first and the second position with a predetermined kink point and the spring element being formed either as a tension or compression spring, preferably in the form of an elastic strip or a coil spring, or as a bending spring, preferably in the form of a leaf spring or a spring beam, mounted and/or aligned between the first and the second position such that in a tensioned position outside the idle position the spring element exerts a force upon the dwell tube at the second position, which force acts at least partially normal to the longitudinal axis of the dwell tube so as to bias the latter from a slightly or not kinked position into the kinked position.

BRIEF DESCRIPTION OF THE DRAWING FIGURES

In the following the invention will be described by way of preferred embodiments, wherein features of different embodiments can be exchanged for and/or combined with each other. It is understood that details of the described preferred embodiments do not restrict the invention as such and various changes, modifications and/or equivalents all of which as such are within the scope of protection of the invention may result obviously for those skilled in the art. Moreover, in the following description of the preferred embodiments like reference numerals are used for corresponding features which may be described only once but may be provided in each of the presented embodiments.

Figure 2:
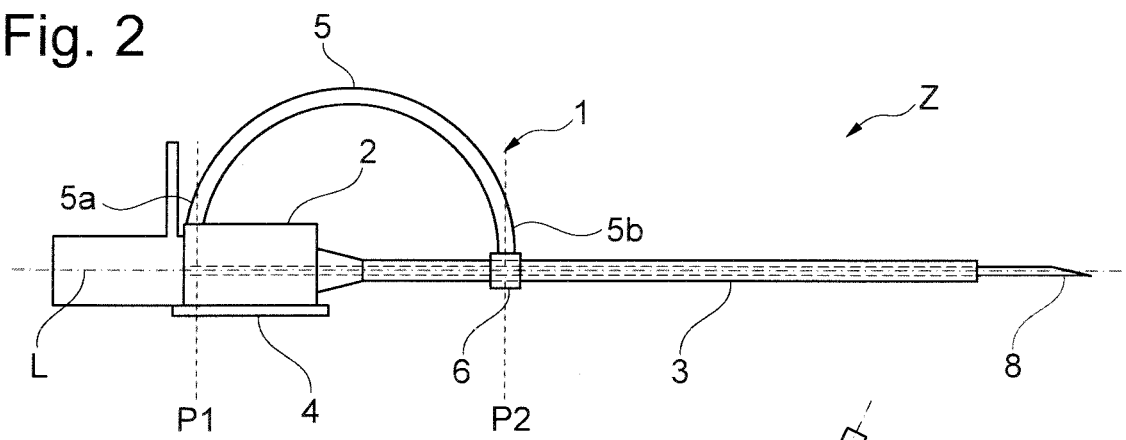
Figure 3:
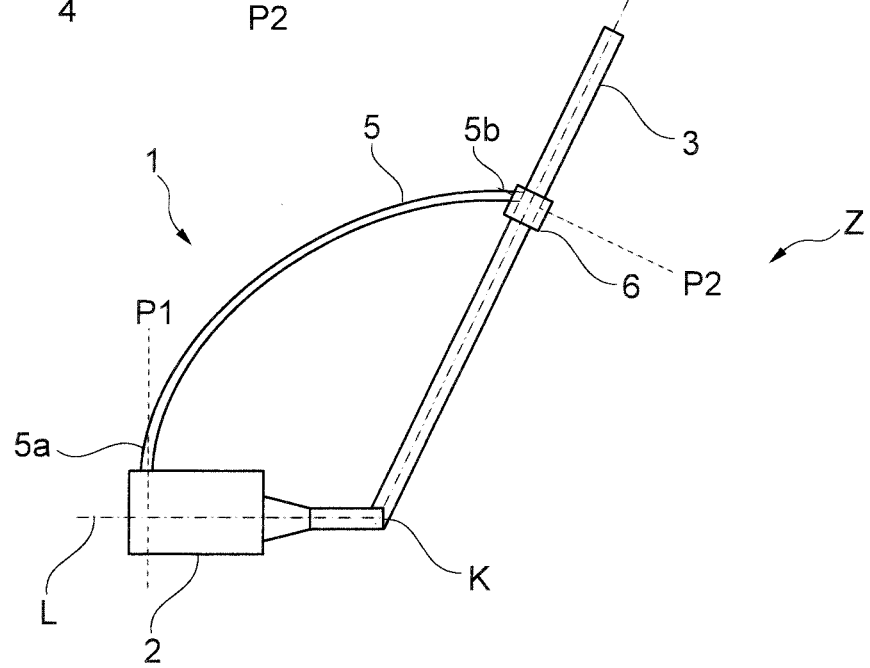
Figure 4:
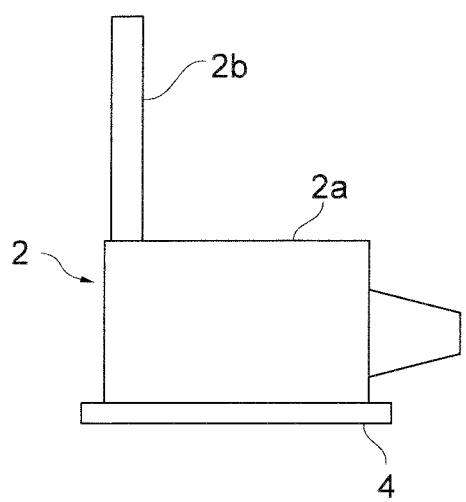
Figure 5:
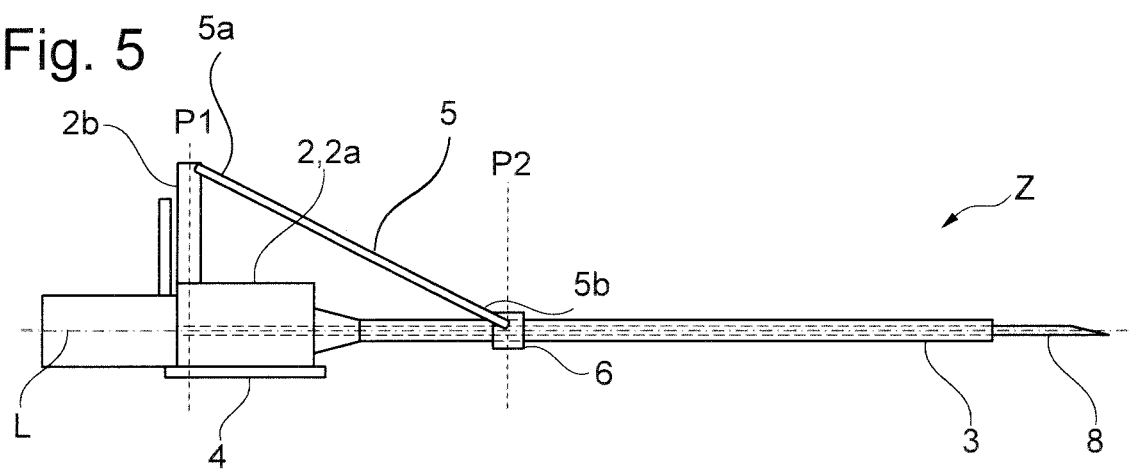
Figure 6:
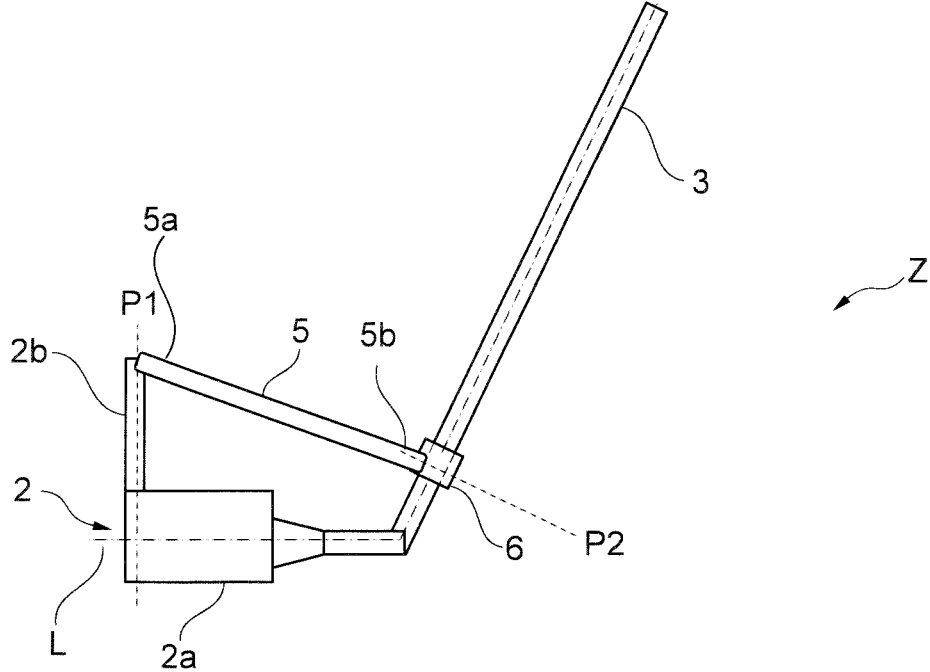

FIG. 1 shows a blocking device according to a first embodiment of the invention in a relaxed position, FIG. 2 shows an access cannula according to the first embodiment which is guided on an insertion needle, FIG. 3 shows an access cannula according to the first embodiment which is in the idle position, FIG. 4 shows part of an access cannula according to the second embodiment, FIG. 5 shows an access cannula according to a second embodiment which is guided on an insertion needle, and FIG. 6 shows an access cannula according to the second embodiment which is in the idle position.

DETAILED DESCRIPTION

FIG. 1 illustrates a blocking device 1 of an access cannula Z according to a first embodiment of the invention. Accordingly, the entire blocking device 1 is integrally formed, wherein all of its elements may be made from the same material, preferably by injection molding. The blocking device 1 includes a sleeve-shaped base portion 2 which is provided for being mounted on and slipped onto a dwell tube 3. The base portion 2 is directly and integrally connected to a fixing base 4 of the access cannula Z which serves for fixing the access cannula Z for treatment preferably adhesively to a patient, more exactly to a skin portion of the patient. Furthermore, the blocking device 1 includes a spring element 5 in the form of a bending spring relaxed in the depicted position which is directly and integrally connected to the base portion 5. The spring element 5 is arranged on the side of the base portion 2 radially opposed to the fixing base 4. Furthermore, the blocking device 1 has a fitting portion 6 which is connected directly and integrally to the spring element 5. The fitting portion 6 is configured in sleeve shape having a mounting hole/receiving hole 7 for mounting/receiving the dwell tube 3.

FIG. 2 illustrates the access cannula Z according to the first embodiment in a completely assembled state. This means that the access cannula Z is provided in the state in which it can be used to lay an access for treatment. Accordingly, the dwell tube 3 rests on an insertion needle 8 which serves for puncturing a patient's tissue such as his/her skin and vessels when laying the access. The afore-described blocking device 1 according to FIG. 1 is mounted to the dwell tube 3. The bending spring in the form of the spring element 5 is bent and tensioned and the sleeve-shaped fitting portion 6 is mounted to the dwell tube 3 as the dwell tube 3 has been guided through the mounting hole 7 of the fitting portion 6. Since the spring element 5 strives for a relaxed stretched position, it exerts a force or a moment having a component which is perpendicular to a longitudinal axis L of the dwell tube 3 upon the dwell tube 3 so that in this way kinking of the dwell tube 3 may be provoked where necessary. The fitting portion 6 is freely movable on the dwell tube 3 so that the fitting portion 6 aligns itself along the dwell tube 3 during mounting and no additional setting of the spring element 5 is required. Since the dwell tube 3 rests on the insertion needle 8 taking the shape of a long straight thin sleeve, the shape of the dwell tube 3 is adapted to the shape of the insertion needle 8, i.e. the dwell tube 3 is maintained in a stretched position by the insertion needle 8.

When laying the access, the insertion needle 8 of the access cannula Z is introduced to the patient's vessel. Then the dwell tube 3 is inserted via the insertion needle 8 into the vessel and the access cannula Z is fixed to the patient's skin. Subsequently, the insertion needle 8 is withdrawn and removed, while the dwell tube 3 remains in the patient's vessel and serves as an access during treatment.

FIG. 3 illustrates the access cannula Z according to the invention in accordance with the first embodiment in an idle position which is given when the dwell tube 3 is not maintained in a stretched position. This is the case, for example, when VND occurs, viz. when the dwell tube 3 of the venous access of the patient slips out of the patient's vessel. In said idle position, the dwell tube 3 is maintained kinked by the force applied by the spring element 5 and the moment thereof, with the kink being provided at a predetermined kink point K of the dwell tube 3 between the first position P1 and the second position P2, viz. between the base portion 2 and the fitting portion 6. The spring element 5 is biased and is balanced with an elastic reset force of the dwell tube 3. Should VND be given, the force of the spring element 5 acts both against the reset force of the dwell tube 3 and against a blood pressure built up in the dwell tube 3.

FIG. 4 illustrates part of a blocking device 1 according to a second embodiment of the invention. It consists of a base portion 2 including a sleeve part 2a which substantially corresponds to the afore-described base portion 2 according to the first embodiment and is also integrally connected to a fixing base 4. Moreover, the base portion 2 according to the second embodiment includes a rod-shaped spacer part 2b extending radially outwardly in a direction normal to the longitudinal axis L of the dwell tube 3, with the spacer part 2b and the sleeve part 2a being formed integrally with each other. The spacer part 2b has a first radially internal end at which it is directly connected to the sleeve part 2a and a second radially external end which is adapted to hold a spring element 5. For this purpose, the second radially external end includes e.g. a notch, an eye or the like into which the spring element 5 can be easily inserted with its first end.

FIG. 5 illustrates the access cannula Z according to the second embodiment in a completely mounted state which substantially corresponds, especially with respect to an applicability as an access for treatment and to the laying thereof and the interaction with an insertion needle 8, to the first configuration set forth in FIG. 2. In contrast to the first embodiment, in the blocking device 1 according to the invention of the access cannula Z in accordance with the first embodiment the spring element 5 is in the form of a tension spring, especially of an elastic strip. Said spring element 5 at its first end 5a includes a portion which forms e.g. a loop, a hook or a T-piece and which is adapted to interact with the second radially external end of the spacer part 2b and can be inserted, hooked into the latter or laid around the latter. In this way, as shown in FIG. 5, the first end 5a of the spring element 5 is held by the second radially external end of the spacer part 2b and thus by the base portion 2. The radial extension of the spacer part 2b or a length thereof defines the distance of the first end 5a of the spring element 5 from the longitudinal axis L of the dwell tube 3.

A second end 5b of the spring element 5 is provided with a portion shaped similarly or equally to the first end 5a of the spring element 5 and is adapted to be held by a fitting portion 6 of the blocking device 1. For this purpose, the substantially sleeve-shaped fitting portion 6 has, similarly to the second radially external end of the spacer part 2b, an appropriately adapted portion, for example including a notch, an eye or the like, by which the second end 5b of the spring element 5 is held. The fitting portion 6 is substantially configured as a sleeve pushed onto the dwell tube 3 which is held and secured against displacement toward the base portion 2 at a position having a predetermined distance from the base portion 2 so that the spring element 5 is tensioned between the base portion 2 and the fitting portion 6. The fitting portion 6 is held by a step formed at the dwell tube 3 or is adhesively fixed to the dwell tube. As an alternative, also a clamping connection may be used, the fitting portion 6 may consist of a simple groove or flute in the dwell tube 3 or the fitting portion 6 may be directly attached to the dwell tube 3 by injection molding or may be manufactured integrally with the same. The force exerted on the dwell tube 3 by the spring element 5 depends and may be adjusted by way of the elasticity and the length of the spring element 5, the radial distance of the first end 5a of the spring element 5 from the longitudinal axis L of the dwell tube 3 as well as the distance of the fitting portion 6 from the base member 2.

FIG. 6 illustrates the access cannula Z according to the invention in accordance with the second embodiment in an idle position which substantially corresponds to the representation of the first example configuration described already in FIG. 3. In this case, too, the spring element 5 exerts a force having at least one component perpendicular to the dwell tube 3 and applies a moment to the latter and maintains the latter in a position kinked at a predetermined kink point K.

The invention claimed is:

1. An access cannula comprising:
   a dwell tube that defines a longitudinal axis along the center of the dwell tube, the dwell tube configured to serve as an access during treatment in a stretched position; and
   a blocking device configured to maintain the dwell tube kinked in an idle position, wherein:
   the blocking device includes a spring element which is arranged with a first end at a first position of the dwell tube and which is connected or connectable with a second end at a second position on the dwell tube,
   the second position is spaced from the first position by a first distance measured along the longitudinal axis of the dwell tube when the dwell tube is in the stretched position,
   the second position is spaced from the first position by a second distance measured along the longitudinal axis of the dwell tube when the dwell tube is kinked in the idle position, and
   the second distance is greater than the first distance, such that the second end of the spring element moves away from the first end of the spring element along the longitudinal axis of the dwell tube as the dwell tube transitions from the stretched position to the idle position.

2. The access cannula according to claim 1, wherein the first distance and the spring element are adjusted so that the spring element is tensioned when the dwell tube is maintained in the stretched position.

3. The access cannula according to claim 1, wherein at the second position the spring element exerts a spring force upon the dwell tube, in which the spring force acts at least partly normal to the longitudinal axis of the dwell tube when the spring element is tensioned.

4. The access cannula according to claim 1, wherein the dwell tube is kinked by a spring force of the spring element when the dwell tube is not maintained in the stretched position.

5. The access cannula according to claim 1, wherein the blocking device further includes a base portion which either directly or indirectly connects or renders connectable the first end of the spring element to the dwell tube and includes a fitting portion which connects or renders connectable the second end of the spring element to the dwell tube.

6. The access cannula according to claim 5, wherein at least the base portion and/or the fitting portion are formed integrally with the dwell tube or as a component different from the dwell tube.

7. The access cannula according to claim 5, wherein the base portion is configured so that the first end of the spring element is connected or connectable at the base portion at a predetermined radial distance from the longitudinal axis of the dwell tube.

8. The access cannula according to claim 1, wherein the spring element is in the form of a bending spring.

9. The access cannula according to according to claim 1, wherein the spring element is in the form of a tension spring.

10. The access cannula according to claim 9, wherein the second position of the dwell tube at which the second end of the tension spring is held has a predetermined minimum distance from the first position or is arranged at the dwell tube at a predetermined axial distance from the first position.

11. The access cannula according to claim 1, wherein the dwell tube at the first position includes a fixing base or a fixing pad configured for fixing of the dwell tube to a patient's surface and on which the spring element is fixed or held at the first end thereof, and the dwell tube at the second position includes a fitting element or a fitting portion at which the spring element is fixed or held at the second end thereof, wherein the dwell tube is formed axially between the first and second positions with a predetermined kink point.

12. The access cannula according to claim 1, wherein the blocking device comprises
a base portion having an open proximal end configured to receive the dwell tube with an insertion needle inside the dwell tube for inserting the dwell tube into a patient.

13. The access cannula according to claim 1, further comprising
an insertion needle configured for insertion through an open proximal end of the dwell tube and into the dwell tube, the insertion needle having a distal end configured to project out of an open distal end of the dwell tube.

14. The access cannula of claim 13, wherein the base portion comprises a first side and a second side opposite the first side.

15. The access cannula of claim 14, wherein the spring element is attached to the first side of the base portion.

16. The access cannula of claim 15, wherein the second side comprises a fixing base for fixing the access cannula to a patient, the fixing base located on the base portion opposite the spring element.

17. The access cannula of claim 13, wherein the insertion needle comprises a proximal end opposite the distal end, the proximal end of the insertion needle configured to reside inside the base portion when the distal end of the insertion needle projects out of the open distal end of the dwell tube.

* * * * *